US00PP13426P2

(12) United States Plant Patent
Olesen et al.

(10) Patent No.: US PP13,426 P2
(45) Date of Patent: Dec. 31, 2002

(54) MINIATURE ROSE VARIETY 'POULBREZ'

(76) Inventors: L. Pernille Olesen, Hillerødvejen 49, DK-3480, Fredensborg (DK); Mogens N. Olesen, Hillerødvejen 49, DK-3480, Fredensborg (DK)

( * ) Notice: Subject to any disclaimer, the term of this patent is extended or adjusted under 35 U.S.C. 154(b) by 48 days.

(21) Appl. No.: 09/676,599

(22) Filed: Sep. 27, 2000

(51) Int. Cl.[7] ..... A01H 5/00

(52) U.S. Cl. ..... Plt./121

(58) Field of Search ..... Plt./121, 128, 116

(56) References Cited

PUBLICATIONS

UPOV–ROM, 2001/04, Plant Variety Database, GTI Jouve Retrieval Software, citation for 'POULbrez'.*

Community Plant Variety Office. "Certificate on the Grant of Community Plant Variety Rights" Jun. 19, 2000. 6 pages. EU.

* cited by examiner

*Primary Examiner*—Howard J. Locker

(57) ABSTRACT

A new miniature rose plant which has abundant, pink flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE INVENTION

The present invention constitutes a new and distinct variety of miniature rose plant which originated from a controlled crossing between an unnamed seedling and an unnamed seedling. The two parents were crossed and the resulting seeds were planted in a controlled environment. The new variety is named 'POULbrez'.

The new rose may be distinguished from its seed parent, an unnamed seedling, by the following combination of characteristics:

1. The unnamed seed parent has peach intonations, which 'POULbrez' does not.

The new variety may be distinguished from its pollen parent, an unnamed seedling, created by the same inventors, by the following combination of characteristics:

1. The unnamed pollen parent has peach intonations, where 'POULbrez' has none.

The objective of the hybridization of this rose variety for commercial culture was to create a new and distinct variety with unique qualities, such as:

1. Uniform and abundant flowers;
2. Vigorous and compact growth;
3. Year-round flowering under glasshouse conditions:
4. Suitability for production from softwood cuttings in pots;
5. Durable flowers and foliage which make a variety suitable for distribution in the floral industry.

The combination of qualities of this variety represents significant improvement over previously available commercial cultivars of this type and distinguishes 'POULbrez' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark in May of 1995.

'POULbrez' was selected by the inventors as a single plant from the progeny of the hybridization in Fredensborg, Denmark in May of 1996.

Asexual reproduction of 'POULbrez' by cuttings and traditional budding was first done by L. Pernille and Mogens N. Olesen in August, 1996, in their nursery in Fredensborg, Denmark. This initial and other subsequent propagations conducted in controlled environments have demonstrated that the characteristics of 'POULbrez' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULbrez'. Specifically illustrated in Sheet 1:

1. Stem showing branching and the attachment of leaves, buds, and peduncles;

2. Flower bud, partially opened bud, and open bloom;

3. Flower petals, detached;

4. Sepals and pedicel;

5. A bare stem and a stem with foliage;

6. Leaves.

DETAILED DESCRIPTION OF THE VARIETY

The following is a description of 'POULbrez', as observed in its growth in glasshouses in Half Moon Bay, Calif. Color references are made using The Royal Horticultural Society (London, England) Colour Chart, 1995, except where common terms of color are used.

For a comparison, several physical characteristics of the rose variety 'POULfuna', a miniature rose variety from the same inventors described and illustrated in U.S. Plant Pat. No. 10,628 and issued on Oct. 6, 1998 are compared to 'POULbrez' in Chart 1.

CHART 1

| | 'POULbrez' | 'POULfuna' |
|---|---|---|
| Bud color at 1/4 open. | Red Group 48 C–D. | Red-Purple Group 53D. |
| Petal color, upper surface. | Red Group 38D. | Red-Purple Group 57B. |
| Petalage | 28 to 32 petals under normal conditions. | 30 to 35 petals under normal conditions. |

Parents: Unnamed seedling×unnamed seedling.
Classification:
*Botanical.*—*Rosa hybrida.*
*Commercial.*—Miniature.

FLOWER AND FLOWER BUD

Blooming habit: Recurrent.
Flower bud:
*Size.*—Upon opening, 17 mm–18 mm in length from base of receptacle to end of bud.
*Bud form.*—Short and globular.
*Bud color.*—As sepals unfold Red Group 48C and 48D; Red Group 48C and 48D at ¼ opening.
*Sepals.*—Yellow-Green Group 144B with intonations of Yellow-Green Group 144A. Weak foliaceous appendages on three of the five sepals. Surfaces of sepals slightly pubescent. Stipitate glands are present on edges of sepals.
*Receptacle.*—Surface: Smooth. Shape: Funnel-shaped. Size: 6 mm (h)×5 mm (w). Color: Yellow-Green Group 144A.
*Peduncle.*—Surface: Moderate number of stipitate glands present. Length: 15 to 20 mm average length. Color: Yellow-Green Group 144A.
*Borne.*—Generally with one bud per flowering stem.
Flower bloom:
*Fragrance.*—None.
*Duration.*—As a pot plant, flowers last from 4 to 5 days. As a cut flower 2 to 3 days.
*Size.*—Small for a 6 cm pot rose. Average flower diameter is 30 mm when open.
*Form.*—Shape of flower when viewed from the side: Upon opening, upper part: Convex. Upon opening, lower part: Flattened convex. Open flower, upper part: Convex. Open flower, lower part: Flat.
*Petalage.*—Average range: 28 to 32 petals under normal conditions with 4 to 6 petaloids.
Color:
*Upon opening, petals.*—Outermost petals: Upper Surface: Margin and middle zone are Red Group 38B, fading to Red Group 38D at the base. Reverse Side: Margin is Red-Purple Group 62B. Middle zone is Red-Purple Group 62D. Innermost petals: Upper Surface: Red Group 38C–D. Reverse Side: Red-Purple Group 62A.
*Upon opening, basal petal spots.*—Outermost petals: Outer Side: Green-Yellow Group 1B. Inner Side: Green-Yellow Group 1B. Innermost petals: Outer Side: Yellow Group 3A. Inner Side: Yellow Group 3A.
*After opening, petals.*—Outermost petals: Upper Surface: Red Group 38D. Reverse Side: Red-Purple Group 62B–C. Innermost petals: Upper Surface: Red Group 38 C–D. Reverse Side: Red-Purple Group 62A.
*After opening, basal petal spots.*—Outermost petals: Outer Side: Green-Yellow Group 1B. Inner Side: Green-Yellow Group 1B. Innermost petals: Outer Side: Green-Yellow Group 1B. Inner Side: Green-Yellow Group 1B.
General tonality: On open flower, Red Group 38C. No change in the general tonality at the end of the 5th day. Afterwards, general tonality is Red Group 38D.
Petals:
*Petal reflex.*—Petals reflex strongly.
*Petal edge.*—Petals have point in center.
*Shape.*—Ovoid.
*Petaloids.*—4 to 6 under normal conditions.
*Thickness.*—Thin.
*Arrangement.*—Imbricated.
Reproductive organs:
*Pollen.*—Color: Yellow-Orange Group 20A. Abundance: Limited.
*Anthers.*—Size: Small. Color: Greyed-Yellow Group 161C. Abundance: Average.
*Filaments.*—Color: Yellow Group 6A at base, fading to Yellow-Orange Group 21B immediately beneath anther.
*Stigmas.*—Slightly superior and occasionally level relative to anthers. Color: Red-Purple Group 61B.
*Styles.*—Color: Red-Purple Group 61B.

PLANT

Plant growth: Vigorous, compact. When grown in a 6 cm pot, as is typical in production of the variety, the average height of the plant is 10 to 12 cm and the average width is 9 to 11 cm.
Stems:
*Color.*—Young wood: Yellow-Green Group 144A–B. Older wood: Yellow-Green Group 144A–B.
*Prickles.*—Incidence: 1 to 4 per 10 cm of stem. Size: Average length: 2 mm–3 mm. Color: Greyed-Yellow Group 160C. Shape: Linear.
*Surface.*—Young wood: Smooth. Older wood: Smooth.
Plant foliage: Normal number of leaflets on leaves in middle of the stem: 5 leaflets.
*Leaf size.*—18 mm (l)×15 mm (w).
*Quantity.*—Very abundant.
*Color.*—Upper Leaf Surface: Green Group 137A. Lower Leaf Surface: Green Group 138B. Juvenile foliage: Upper surface: Green Group 137A. Lower surface: Green Group 138B.
Plant leaves and leaflets:
*Stipules.*—Size: 5 mm–8 mm. Color: Yellow-Green Group 145B–C. Presence of stipitate glands: Present.
*Petiole.*—Length: 5 mm–7 mm. Color: Yellow-Green Group 144C. Margins: Green Group 137A.
*Rachis.*—Color: Yellow-Green Group 144A. Underneath: Yellow-Green Group 144B. Margins: Yellow-Green Group 144B.
*Leaflet.*—Edge: Serrated. Shape: Ovate. Other: Moderately glossy.
Disease resistance: Average resistance to mildew, black spot, and Botrytis under normal growing conditions in Half Moon Bay, Calif.
Cold hardiness: 'POULbrez' has been found to be resistant to damage from cold, heat and drought damage in USDA Zone 7 .

We claim:

1. A new and distinct variety of rose plant of the miniature class, substantially as herein illustrated and described as a distinct and novel rose variety due to its abundant, pink flowers, vigorous and compact growth, year round flowering under glasshouse conditions, suitability for production form softwood cuttings in pots, and durable flowers and foliage which make the variety suitable for distribution in the floral industry.

* * * * *

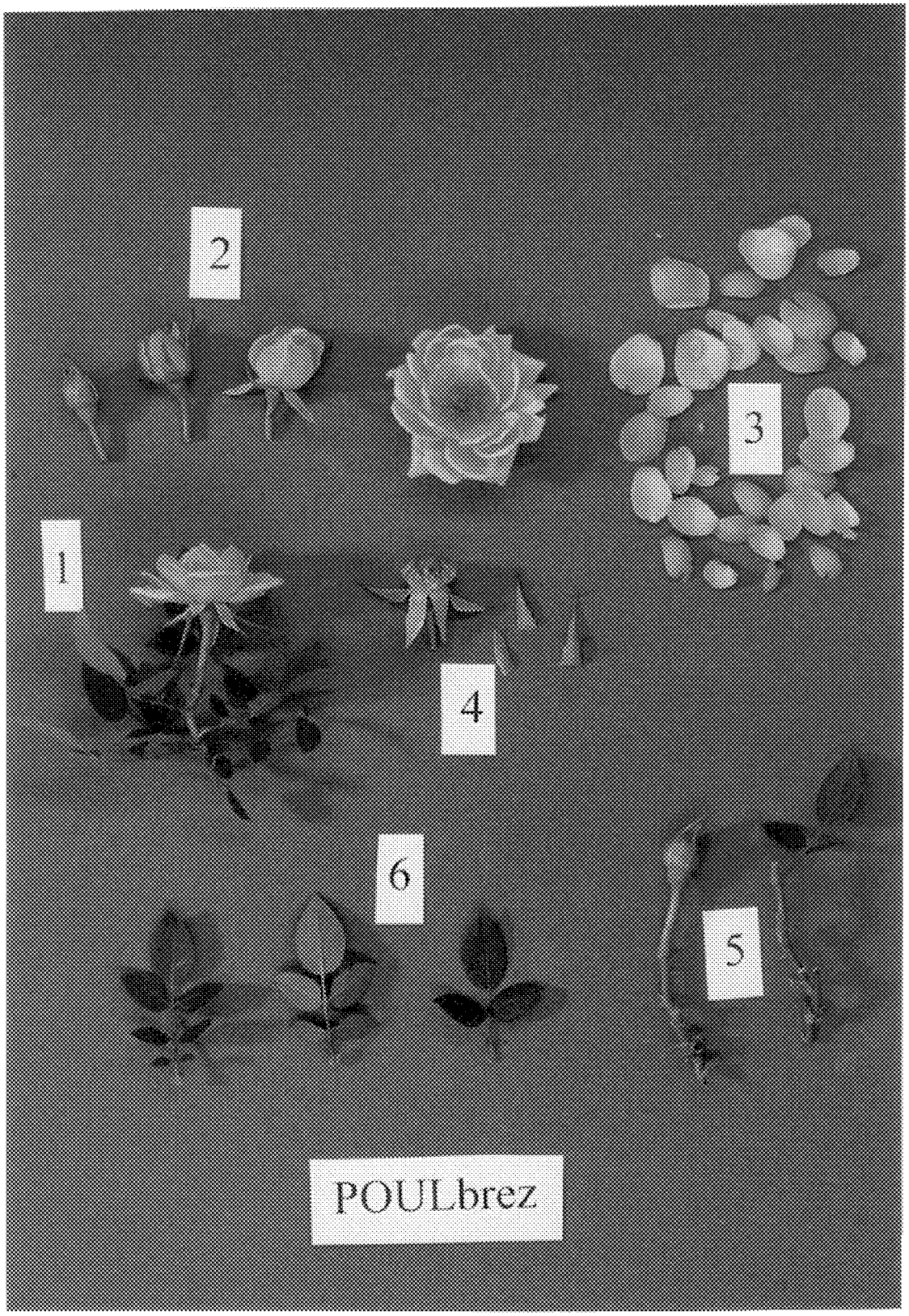
2
3
1
4
6
5
POULbrez